United States Patent [19]

Sigl

[11] Patent Number: 4,582,550
[45] Date of Patent: Apr. 15, 1986

[54] METHOD OF MAKING AN ELASTICIZED GARMENT

[75] Inventor: Wayne C. Sigl, Winnebago County, Wis.

[73] Assignee: Kimberly-Clark Corporation, Neenah, Wis.

[21] Appl. No.: 713,222

[22] Filed: Mar. 18, 1985

Related U.S. Application Data

[62] Division of Ser. No. 430,623, Sep. 30, 1982, Pat. No. 4,527,990.

[51] Int. Cl.⁴ .................... A61F 13/16; B32B 31/04; B32B 31/26
[52] U.S. Cl. ...................................... 156/84; 156/85; 428/230; 604/385 A
[58] Field of Search ................ 156/84, 85, 205, 206; 264/230, 342 R; 428/230; 604/385 A

[56] References Cited

U.S. PATENT DOCUMENTS

| | | | |
|---|---|---|---|
| 3,089,283 | 5/1963 | Kirkpatrick | 156/84 |
| 3,819,401 | 6/1974 | Massengale et al. | 156/85 |
| 3,868,729 | 3/1975 | Lynam | 428/230 |
| 3,912,565 | 10/1975 | Koch et al. | 156/85 |
| 4,498,944 | 2/1985 | Krause et al. | 156/205 |

FOREIGN PATENT DOCUMENTS 3046385  4/1978  Japan ................................. 428/230

*Primary Examiner*—Caleb Weston

[57] ABSTRACT

An elasticized article and a method for elasticizing the article are disclosed in which a strip of elastic material has an end bonded to an end of a strip of shrinkable material to form a single elongated strip having spaced apart opposing ends. The combined strip is bonded at its opposing ends to a flexible substrate of an article with the elastic material in a contracted relaxed condition and the shrinkable means in a stable extended condition. Subsequent to the application of the combined strip to the flexible substrate, the shrinkable means is contracted by shrinking to thereby extend the elastic material and elasticize the flexible substrate.

5 Claims, 9 Drawing Figures

METHOD OF MAKING AN ELASTICIZED GARMENT

This is a divisional of copending application Ser. No. 430,623, filed on Sept. 30, 1982, now U.S. Pat. No. 4,527,990.

FIELD OF THE INVENTION

This invention relates to an elasticized article and a method for elasticizing an article. More particularly, the invention relates to a disposable diaper which is elasticized in the waist area and a method for applying elastic in the waist area of the disposable diaper.

BACKGROUND OF THE INVENTION

Articles for uses such as garments or for protective packaging are frequently elasticized to provide a sealed tight fit. Among the various types of garments using elastic means to provide a sealed fit are disposable garments such as disposable diapers which are often sealed in the leg area to prevent leakage of body excretions. There has also been an increased interest in sealing the waist area of disposable diapers for the same purpose.

There are several ways that articles may be elasticized. These include the sewing of elastic into the substrate material which is to form the article, adhering the elastic onto the substrate material, and utilizing a heat shrinkable elastic which is bonded to the article and shrunk by the application of heat to an elastic form which permits the elastic extension and contraction of the substrate. Sewing of elastic into disposable articles is presently seldom used due to its complexity and slowness and resulting high cost. Adhering of the elastic onto a substrate material is commonly used, but nevertheless has its drawbacks. These include the difficulty of handling the elastic in a stretched form, particularly when it is applied in a direction transverse to the direction of movement of a moving substrate material. When elastic is glued to a substrate material in a relaxed condition, it is necessary to first corrugate the substrate material so that it will have excess material with can be extended to stretch the elastic and provide the elasticization effect. The need to corrugate the substrate material also complicates this approach, particularly when the elastic is applied in a direction transverse to the direction of a moving substrate material. Heat shrinkable elastic is applied in a relaxed form and, because it will gather the substrate material with it when it is caused to shrink, it is not necessary that the substrate material first be corrugated. The application of the heat shrinkable elastic in a relaxed form and the elimination of the need to corrugate the substrate material simplifies this approach considerably. However, the temperature level required to shrink the heat shrinkable elastic is above the tolerance level of some substrate materials commonly used in making disposable garments, particularly polypropylene and polyethylene films, and so it is difficult to use heat shrinkable elastic with these substrates. Moreover, heat shrinkable elastics often do not retain a sufficient amount of their elastomeric properties when heated and they thus are frequently unsuitable for many elasticization purposes.

SUMMARY OF THE INVENTION

It is a principal object of this invention to provide an elasticized article and a method for making the elasticized article on a high speed production basis with none of the drawbacks of presently known elasticized articles and methods for their fabrication. It is a more specific object of this invention to provide a method of elasticizing an article in which the elastic can be applied in a relaxed condition without having the substrate material in a corrugated condition. It is a further specific object of this invention to provide an elasticized article in which the elastic material and shrinkable material are separate but connected together and the shrinkable material applies tension to the elastic material.

According to the invention, an elasticized article is provided which includes a flexible substrate, elastic material having a surface area and which is bonded to the substrate over less than the surface area of the elastic material, and shrinkable means having a surface area and which is bonded to the substrate over less than the surface area of the shrinkable means and bonded to the elastic material over a surface area that is less than the surface area of the shrinkable means or the elastic material, the shrinkable means providing a force along a direction between the area of the bond of elastic material to the substrate and the area of the bond of the shrinkable means to the substrate for gathering the substrate upon shrinking whereby, when the substrate is extended, the elastic material applies gathering force to the substrate. The shrinkable material may be responsive to a stimulus such as heat or moisture to shrink to a smaller form such that the elastic material is extended to thereby apply elastic contracting force to the flexible article. Note that the term "elasticized" as used herein means the provision of an elastic contracting force to the article.

DESCRIPTION OF THE DRAWINGS

Further objects and advantages of the invention will appear when taken in conjunction with the accompanying drawings in which.

DETAILED DESCRIPTION OF THE INVENTION

Figure 1:
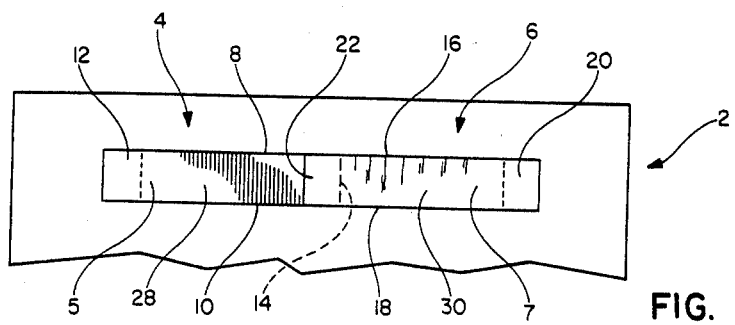
FIG. 1 is a plan view of a portion of an elasticized article according to the invention.

Referring generally to FIGS. 1-4, an elasticized article is shown which includes a flexible substrate 2, an elastic material 4 and shrinkable means 6. The elastic material 4 preferably is in the shape of a strip 5 with a length dimension greater than the width dimension. The elastic material 4 as illustrated in FIGS. 1-4 includes longitudinal edges 8 and 10, opposing ends 12 and 14, a surface area 24 facing the flexible substrate, and a surface area 28 facing away from flexible substrate 2. The shrinkable means 6 comprises a shrinkable material, preferably in the shape of a strip 7 in which the length dimension is greater than the width dimension. The shrinkable means 6 has longitudinal edges 16 and 18, opposite ends 20 and 22, a surface area 26 facing the flexible substrate 2, and a surface area 30 facing away from flexible substrate 2.

A first portion of the surface area 24 of elastic material 4, preferably the end area 12, is bonded to the flexible substrate 2 and a second portion of the surface area 24, preferably the end area 14, is bonded to the surface area 26 of shrinkable means 6, preferably at end area 22. A portion of the surface area 26 of shrinkable means 6, preferably the end area 20, is bonded to the flexible substrate 2. It is important that the elastic material 4 and the shrinkable means 6 are bonded to the substrate 2 at different locations and over surface areas that are less than their entire surface areas to permit the tensioning of the elastic material and the contracting of the shrinkable means without constriction by the substrate and between the bonded locations.

The flexible substrate 2 may comprise a wide variety of materials, depending on the ultimate use of the elasticized article, and will typically be of a material that can be provided in a thin film form. Preferred materials for fabricating disposable diapers are polyethylene film having a maximum thickness of about 5 mils and nonwoven fibrous polypropylene sheeting having a basis weight of from 0.5 to 1.25 oz./yd. The shrinkable means 6 may be of a material which has a stable extended condition, is preferably non-elastomeric, and is responsive to heat to shrink to a relatively stable contacted condition. Suitable materials include heat shrinkable oriented film materials such as ethyl vinyl acetate, polypropylene, polyvinyl chloride, and low density polyethylene. In selecting a heat shrinkable material it is critical that the temperature at which the material shrinks is lower than the heat distortion temperature of the substrate material to which the shrinkable material is bonded. For a polyethylene substrate, the heat distortion temperature is about 250° F.

Figure 2:
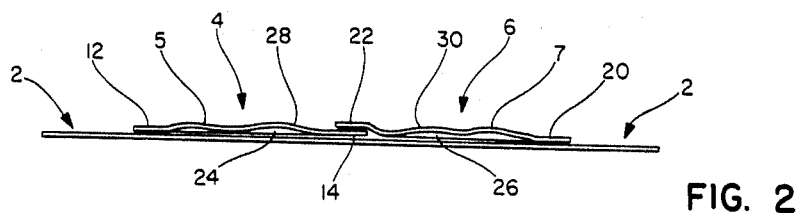
FIG. 2 is an end elevation view of the elasticized article shown in FIG. 1.
Figure 3:
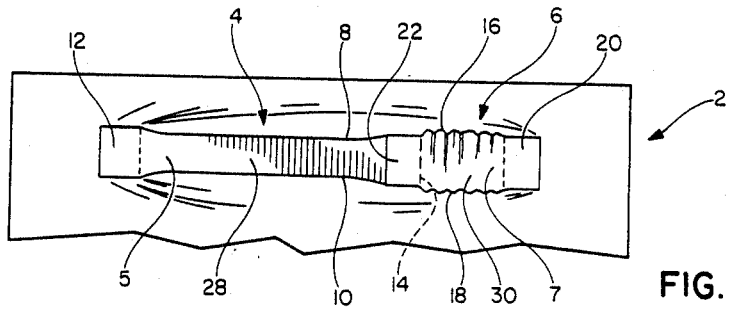
FIG. 3 is a plan view of the elasticized article shown in FIG. 1 with the shrinkable material in a contracted condition and the elastic material in an extended condition.
Figure 4:
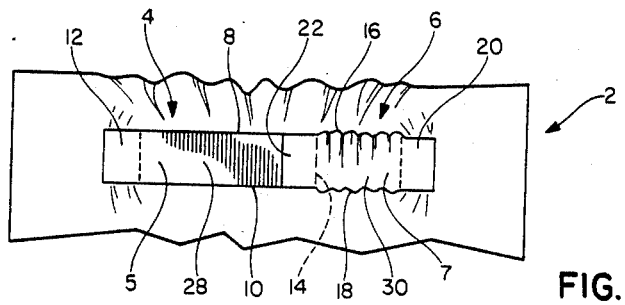
FIG. 4 is a plan view of the elasticized article shown in FIG. 3 with the shrinkable material in a contracted condition, the substrate material gathered, and the elastic material in a relaxed condition.

In the views of FIGS. 1 and 2, the article is shown in a condition in which the flexible substrate 2 is ungathered, the elastic material is 4 is in a relaxed, contracted condition, and the shrinkable means 6 is in a stable, extended condition. In FIG. 3, the flexible substrate 2 is held by means (not shown) in an ungathered condition, the shrinkable means 6 is in a shrunken condition subsequent to its contraction, and the elastic material 4 is in an extended, stretched condition due to the tension applied to it by the contracted shrinkable means 6 while the flexible substrate 2 is held ungathered. Note that the tension force applied by the shrinkable means 6 to the elastic material 4 is along the direction between the location of the bond of the end area 12 of elastic material 4 to the substrate and the location of the bond of the end area 20 of the shrinkable means 6 to the substrate 2. In FIG. 4, the shrinkable means 6 is shown in its contracted condition and the elastic material 4 is in a relaxed, contracted condition. The flexible substrate 2 is in a gathered condition due to the contracting force applied to it by the elastic material 4 through the bonded end area 12 of the elastic material 4 and the bonded end area 20 of the shrinkable means 6.

Figure 9:
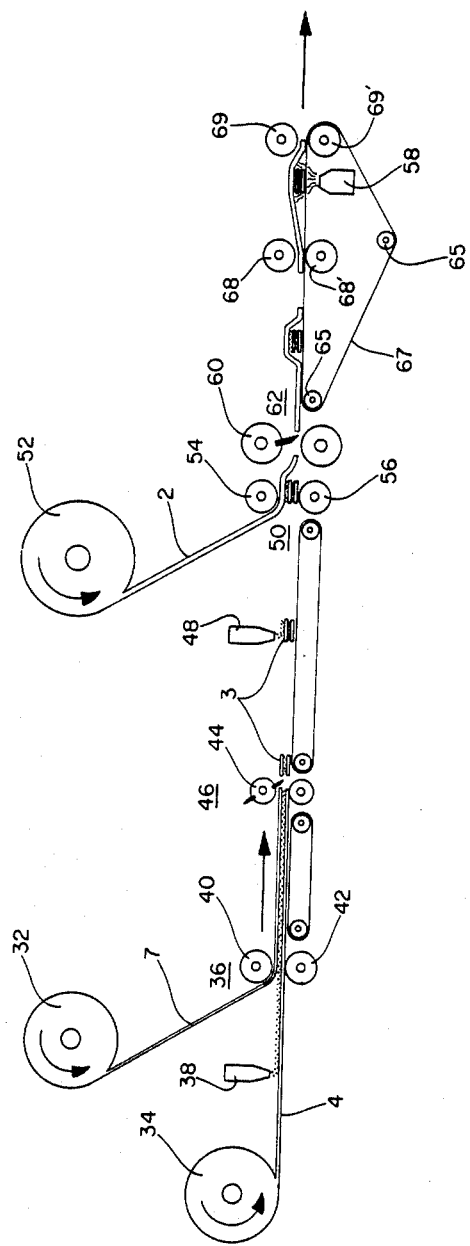
FIG. 9 is a schematic side elevation view of apparatus for elasticizing an article according to the invention.

The elasticized article may be made, as illustrated in FIG. 9, by feeding a roll 32 of continuous shrinkable material and a roll 34 of continuous elastic material 4 to a combining station 36 with the elastic material 4 in a relatively relaxed condition and applying adhesive to the elastic material 4 with an adhesive applicator means 38. The rolls 32 and 34 are positioned such that the shrinkable material and elastic material are overlapped only along one longitudinal edge of each material at the combining station 36. The adhesive is applied to either the elastic material or the shrinkable material in the overlapped area. The overlapped area is then passed between nip rolls 40 and 42 to bond the shrinkable material and elastic material together along the overlapped margins. The combined shrinkable material and elastic material 4 is then severed by cutting means 44 at cutting station 46. The severed strips of combined shrinkable material strips 7 and elastic material strips 5 each have adhesive applied to their respective end areas 12 and 20 by adhesive applicator means 48 and the combined strips are then moved on to an application station 50 where they engage a continuous web of flexible substrate 2. The flexible substrate 2 is supplied from a roll 52 on to a continuous moving screen 67 which moves continuously around rolls 69' and 65. The strips of combined elastic material 4 and shrinkable material are passed between nip rolls 54 and 56 to bond the end areas 12 and 20 of the elastic material 4 and shrinkable material 6, respectively, to the substrate 2. The web of flexible substrate material 2 may then be severed by cutting means 60 at cutting station 62 into a series of separate web pieces. The shrinkable material 6 may then be subjected to a stimulus, such as heat from a heat source 58, to elevate its temperature and cause it to shrink to a contracted condition and provide elasticized articles according to the invention. However, due to the clamping of the web of flexible substrate 2 by clamping rolls 68, 68' and 69, 69', the web maintains its width and the elastic material strip 5 assumes an extended, tensioned condition as shown in FIG. 3.

An alternative embodiment of the invention is illustrated in FIGS. 5-8 in which the elasticized article is a disposable diaper. Those elements shown in FIGS. 5-8 which are the same as or similar to corresponding elements in the embodiment of FIGS. 1-4 are identified with the same numerals and only those elements in FIGS. 5-8 which are substantially different from or in addition to the elements of FIGS. 1-4 are identified with different numerals. The disposable diaper comprises a flexible substrate in the form of a liquid impervious cover sheet 70, a flexible substrate in the form of a liquid pervious body side liner sheet 72 which is joined to the sheet 70 along the periphery of the two sheets, and an absorbent pad 74 disposed between the sheets 70 and 72. The diaper has a front waist area 64 and a rear waist area 66. The diaper also includes elastic strips 76 and 78 located in the leg area of the diaper for sealing the diaper about the legs when the diaper is being worn, and waist fastening tapes 80 and 82 for securing the diaper around the waist when the diaper is being worn.

Figure 5:
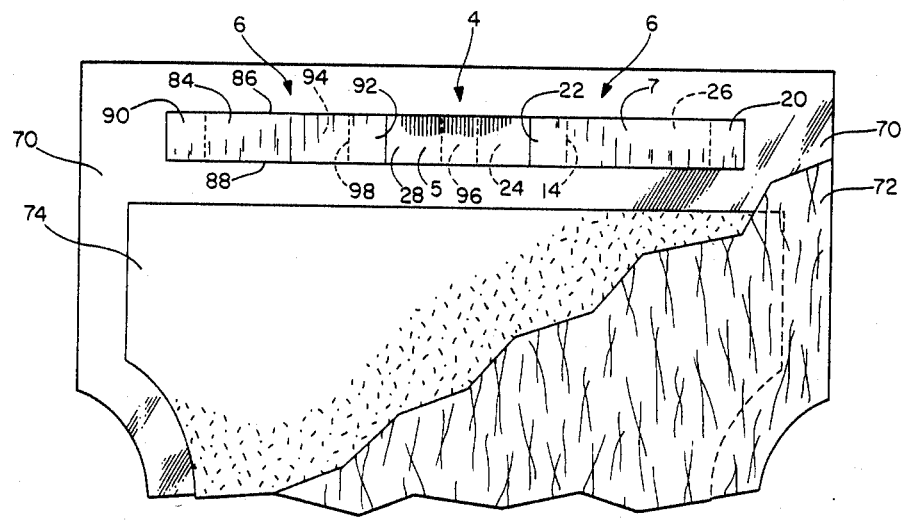
FIG. 5 is a plan view, partially broken away, of an alternative embodiment of the invention in which the elasticized article is a disposable diaper.
Figure 6:
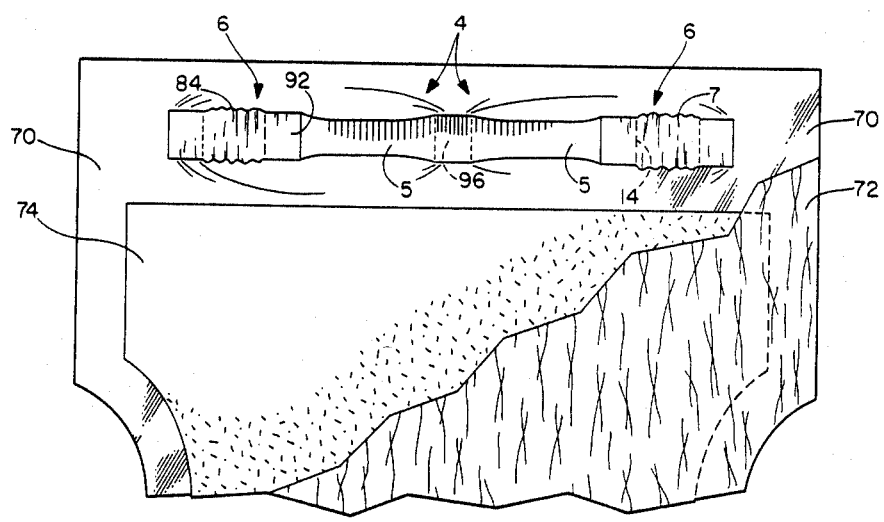
FIG. 6 is a plan view, partially broken away, of the elasticized disposable diaper of FIG. 5 with the shrinkable material in a contracted condition and the elastic material in an extended condition.

As is best illustrated in FIGS. 5 and 6, the shrinkable means 6 includes a shrinkable material strip 7 and a shrinkable material strip 84 having opposite end areas 90 and 92 and surface area 94 facing the cover sheet 70. The elastic material 4 includes elastic strip 5 having opposite end areas 14 and 98 on the surface area 28 facing away from the sheet 70. The strip 5 also has a surface area 24 facing the sheet 70. A portion of the surface area 94 of shrinkable strip 84, preferably the end area 90, is bonded to the cover sheet 70 and a portion of the surface area 94, preferably the end area 92, is bonded to a portion of the surface area 28, preferably end area 98, of elastic strip 5. A portion of the surface area 26 of shrinkable strip 7, preferably the end area 20, is bonded to the cover sheet 70 and a portion of the surface area 26, preferably the end area 22, is bonded to a portion of the surface area 28, preferably end area 14, of elastic strip 5. The elastic strip 5 has a portion 96 of its surface area 24 intermediate its end areas 98 and 14 bonded to the cover sheet 70.

Figure 7:
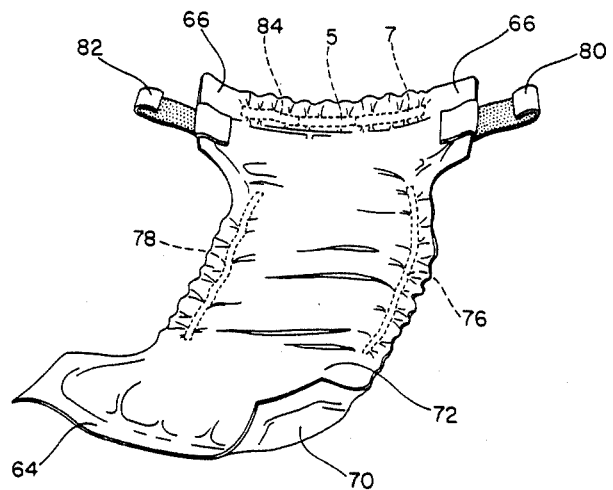
FIG. 7 is a simplified perspective view of the elasticized disposable diaper illustrated in FIGS. 5 and 6, just prior to the fitting of the diaper onto an infant, with an elasticized waist area in a relaxed condition.
Figure 8:
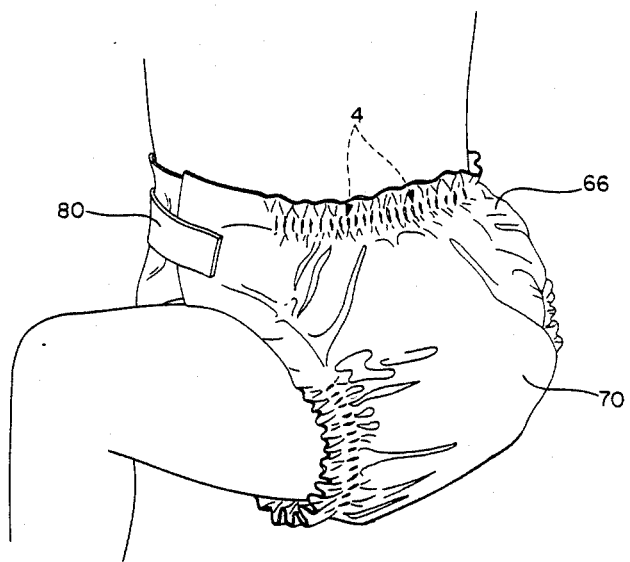
FIG. 8 is a perspective view showing the diaper of FIG. 7 being worn by an infant.

The disposable diaper is illustrated in FIG. 5 with the cover sheet 70 in an extended, ungathered condition, the elastic material strip 5 in a relaxed, contracted condition, and the shrinkable material strips 7 and 84 in a stable, extended condition. In FIG. 6, the cover sheet 70 is in an extended, ungathered condition, the material strips 7 and 84 are in a contracted condition, and the elastic material 4 is in a tensioned, extended condition. Due to the bonding of the elastic material strip 5 at the intermediate area 96, the tension applied to the strip 5 by the shrinkable material strip 7 is between the bonded area 96 and the end area 14 and the tension applied by the strip material 84 is between the bonded area 96 and the end area 92. Where the bonded surface portion 96 is located equidistant between its end areas 92 and 14, the tension applied to the elastic strip 5 will be asymetical about the bonded area 96. In FIG. 7, the diaper is shown in a condition in which cover sheet 70 and the liner sheet 72 attached to its are in a contracted condition, the shrinkable material strips 7 and 84 are in a contracted condition, and the elastic strip 5 is in a contracted, relaxed condition. In FIG. 8, illustrating the diaper being worn by an infant, the waist tapes 80 and 82 have been attached about the waist of the diaper to tension and extend the elastic material 4 so that it is in a condition similar to that shown in FIG. 6 and the tension of the elastic causes a tight seal between the skin of the infant and the liner sheet 72 of the diaper.

It will be understood that the foregoing description of the present invention is for purposes of illustration only and that the invention is susceptible of a number of modifications or changes, none of which entail any departure from the spirit and scope of the present invention as defined in the hereto appended claims.

What is claimed is:

1. A method of elasticizing a flexible article comprising the steps of:
    bonding a portion of an elastic material to the flexible article;
    bonding a portion of a shrinkable material to the flexible article at a distance from the bonded portion of the elastic material;
    bonding a portion of the elastic material to a portion of the shrinkable material intermediate the portions of the elastic material and shrinkable material bonded to the flexible article; and
    shrinking the shrinkable material to decrease the length of the shrinkable material between the portions of the elastic material and shrinkable material bonded to the flexible article whereby, when the article is maintained at said distance, the elastic material applies elastic contracting force to the article.

2. The method according to claim 1 wherein:
    the step of bonding the elastic material and the shrinkable material together is accomplished by bonding an edge of an elongated strip of elastic material to an edge of an elongated strip of shrinkable material; and further comprising the steps of
    severing the combined elastic and shrinkable material strip transversely of its length; and
    maintaining the elastic material in an unextended, relaxed condition while bonding the combined elastic and shrinkable material to the flexible substrate.

3. The method according to claim 2 wherein the step of bonding the elastic material and the shrinkable material to the flexible article is accomplished by bonding the opposite ends of the combined elastic and shrinkable material strip to the flexible article.

4. The method according to claims 1, 2 or 3 further comprising the step of maintaining the distance between the portions of the elastic material and shrinkable material bonded to the flexible article constant while shrinking the shrinkable material.

5. The method according to claim 3 wherein the step of shrinking the shrinkable material is accomplished by elevating the temperature of the shrinkable material.

* * * * *